US009341602B2

(12) United States Patent
Smith et al.

(10) Patent No.: US 9,341,602 B2

(45) Date of Patent: May 17, 2016

(54) ULTRASOUND GENERATING APPARATUS, AND METHODS FOR GENERATING ULTRASOUND

(75) Inventors: Oliver Smith, University Heights, OH (US); Michael R. Sutton, Matlock (GB); Mitchell Peplow, Matlock (GB)

(73) Assignee: The Lubrizol Corporation, Wickliffe, OH (US)

( * ) Notice: Subject to any disclaimer, the term of this patent is extended or adjusted under 35 U.S.C. 154(b) by 140 days.

(21) Appl. No.: 13/977,779

(22) PCT Filed: Jan. 3, 2012

(86) PCT No.: PCT/US2012/020043

§ 371 (c)(1), (2), (4) Date: Apr. 25, 2014

(87) PCT Pub. No.: WO2012/094294

PCT Pub. Date: Jul. 12, 2012

(65) Prior Publication Data

US 2014/0224023 A1 Aug. 14, 2014

Related U.S. Application Data

(60) Provisional application No. 61/430,229, filed on Jan. 6, 2011.

(51) Int. Cl.

| | |
|---|---|
| ***G01N 29/34*** | (2006.01) |
| ***B06B 1/02*** | (2006.01) |
| ***G01S 15/89*** | (2006.01) |
| ***G01N 29/07*** | (2006.01) |
| *A61B 8/00* | (2006.01) |

(52) U.S. Cl.

CPC ............ *G01N 29/346* (2013.01); *B06B 1/0207* (2013.01); *G01N 29/07* (2013.01); *G01S 15/89* (2013.01); *A61B 8/58* (2013.01)

(58) Field of Classification Search

CPC .... B06B 1/0207; G01S 15/89; G01N 29/346; G01N 29/07; A61B 8/58

USPC ............................................................ 73/632

See application file for complete search history.

(56) References Cited

U.S. PATENT DOCUMENTS 5,637,947 A * 6/1997 Kising et al. ............. 310/316.01
6,298,726 B1 * 10/2001 Adachi et al. .................. 73/632

(Continued)

FOREIGN PATENT DOCUMENTS

JP 58-103440 A 6/1983
JP 2004-85370 A 3/2004

OTHER PUBLICATIONS

Written Opinion of corresponding International Application No. PCT/2012/020043 dated May 8, 2012.

(Continued)

*Primary Examiner* — J M Saint Surin

(74) *Attorney, Agent, or Firm* — David M. Shold; Teresan W. Gilbert

(57) ABSTRACT

Ultrasound generating apparatus (10) comprises an arbitrary waveform generator (12) to provide a waveform output at (14), representing a waveform. A power amplifier (16), which may be an operational amplifier, is operable to amplify the waveform output (14) in power and amplitude to provide a power output (18) for applying to an ultrasonic transducer (20).

11 Claims, 2 Drawing Sheets

10
14
18
20
12
16

(56) References Cited

U.S. PATENT DOCUMENTS

| | | | |
|---|---|---|---|
| 7,391,242 | B1 | 6/2008 | Ball |
| 2004/0045356 | A1 | 3/2004 | Dwyer |
| 2004/0227414 | A1* | 11/2004 | Gunnerman et al. ........... 310/26 |
| 2006/0010919 | A1* | 1/2006 | Wang ......................... 65/374.13 |
| 2006/0058677 | A1* | 3/2006 | Okada et al. .................. 600/459 |
| 2007/0068605 | A1 | 3/2007 | Statnikov |
| 2008/0289420 | A1 | 11/2008 | Cochran |
| 2009/0143681 | A1 | 6/2009 | Jurvelin |
| 2009/0206676 | A1 | 8/2009 | Chu |
| 2014/0023556 | A1* | 1/2014 | Jiang ............................... 422/29 |

OTHER PUBLICATIONS

Corresponding International Publication No. WO 2012/094294 A1 published Jul. 12, 2012.

Search Report from corresponding International Application No. PCT/US2012/020043 dated May 8, 2012.

Japanese language document No. 064340, dated Jan. 2, 2008, downloaded from Internet in Feb. 2015.

* cited by examiner

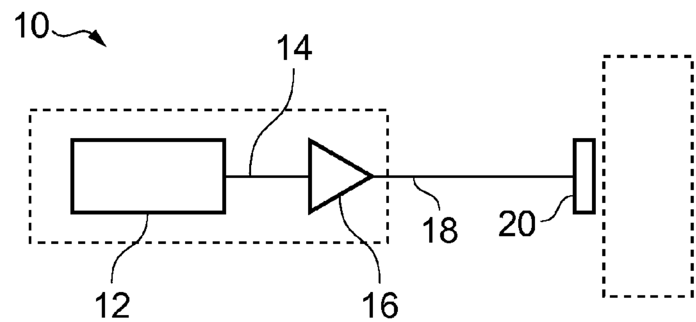
FIG. 1
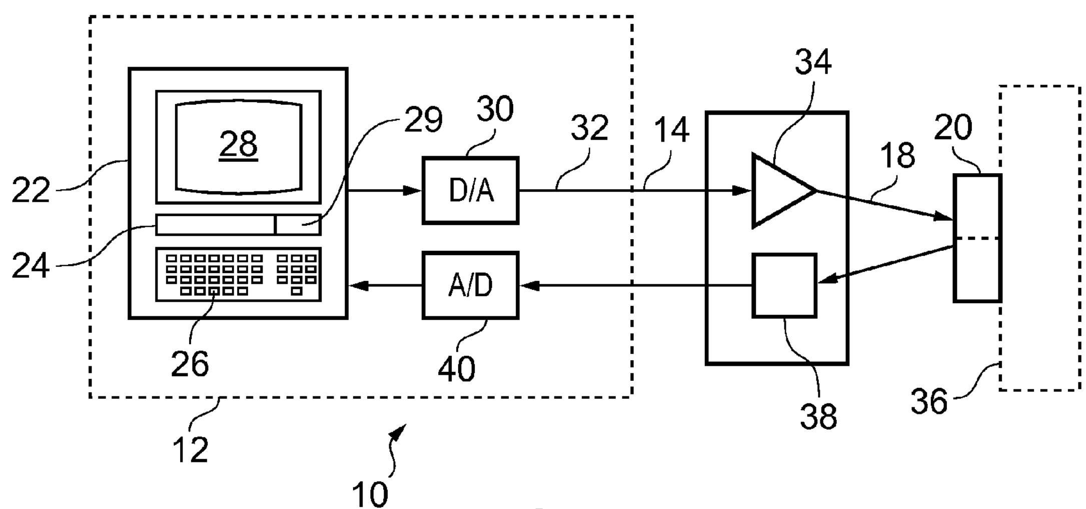
FIG. 2
42
FIG. 3(a)
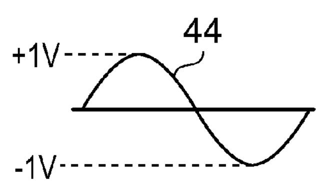
FIG. 3(b)
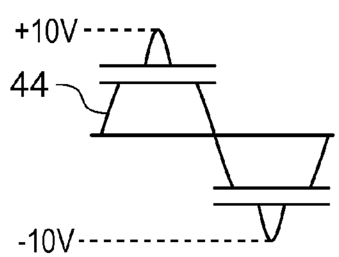
FIG. 3(c)

ULTRASOUND GENERATING APPARATUS, AND METHODS FOR GENERATING ULTRASOUND

The present invention relates to ultrasound generating apparatus and methods for generating ultrasound.

The term "ultrasound" is used to refer to sound at a frequency above the audible range, typically above 20 kHz. Ultrasound has been used for various testing techniques, such as non-destructive testing in which ultrasound is injected into a workpiece and then detected, to reveal information about the workpiece. The nature and quality of the information which can be revealed both depend on the manner in which the ultrasound is generated and used.

Examples of the present invention provide ultrasound generating apparatus comprising:

an arbitrary waveform generator operable to provide a waveform output representing a waveform;

a power amplifier operable to receive the waveform output and to amplify the waveform output in power and amplitude to provide a power output for applying to an ultrasonic transducer.

The power amplifier may comprise an operational amplifier.

The waveform output may, in use, be a time series of discrete output values as samples of the waveform (or having, or constituting the waveform or samples thereof). The discrete outputs may have a sample rate of at least 10 times the frequency of the waveform, such as 100 MS/s when using a 10 MHz transducer. The generator may comprise a waveform source providing a representation of the waveform, user inputs operable to define parameters of the waveform represented, and a converter operable to provide the waveform output as a signal having the waveform of the representation.

The representation may be a digital representation, and the converter may be a digital-to-analogue convertor. The waveform source may be provided by a computing device operating under software control.

The generator may be operable to provide a waveform output as a pulse of a carrier frequency. The generator may be operable to provide a waveform output as a pulse for generating ultrasound and followed by a damping pulse for damping resonance in an ultrasonic transducer.

Examples of the present invention also provide a method of generating ultrasound, comprising the steps of:

generating a waveform output representing a waveform;

amplifying the waveform output in power and amplitude to provide a power output for applying to an ultrasonic transducer.

The waveform output may be amplified by a power amplifier which comprises an operational amplifier.

The waveform output may be generated as a time series of discrete output values as samples of the waveform. The discrete outputs may have a sample rate of at least 10 times the frequency of the waveform, such as 100 MS/s when using a 10 MHz transducer.

Generating the waveform may include providing a representation of the waveform, receiving user inputs to define parameters of the waveform represented, and providing the waveform output as a signal having the waveform of the representation. The representation may be a digital representation and may be provided by a computing device operating under software control. Generating the waveform may include providing a waveform output as a pulse of a carrier frequency. Generating the waveform may include providing a waveform output as a pulse for generating ultrasound and followed by a damping pulse for damping resonance in an ultrasonic transducer.

Examples of the present invention also provide a method of ultrasonic measurement of a dimension of a workpiece, comprising the steps of:

shaping a waveform output to represent a waveform;

applying the shaped waveform output to an ultrasonic transducer to transmit ultrasound into a workpiece;

receiving an ultrasonic signal from the workpiece, the received signal comprising a reflection of the transmitted signal;

extracting information relating to the dimension from the received signal;

wherein the waveform output is shaped and applied by means of apparatus according to any of the preceding definitions.

Examples of the present invention will now be described in more detail, by way of example only, and with reference to the accompanying drawings, in which:

FIG. 1 is a simple schematic diagram of ultrasound generating apparatus in accordance with one example of the invention being described;

FIG. 2 illustrates the apparatus of FIG. 1 in more detail;

FIG. 3 illustrates signals at various points in the apparatus of FIG. 1 and FIG. 2;

OVERVIEW

Figure 4:
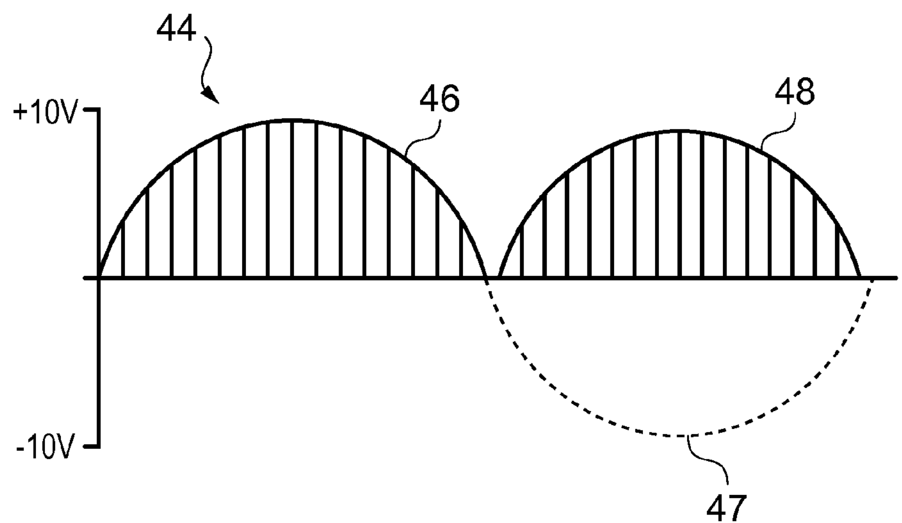
FIG. 4 illustrates another example signal of the type which may be used within the apparatus described.

FIG. 1 illustrates ultrasound generating apparatus indicated generally at 10 and comprising an arbitrary waveform generator 12 operable to provide a waveform output at 14 representing a waveform. A power amplifier 16 is operable to receive the waveform output 14 and to amplify the waveform output 14 in power and amplitude to provide a power output at 18 for applying to an ultrasonic transducer. An example ultrasonic transducer is indicated at 20.

In this specification, the term "arbitrary waveform generator" is used to refer to an arrangement which can produce a waveform output representing any of a very wide range of waveforms defined by the user. Many examples will be known to the skilled reader. These include software packages. One example of software packages which can be used in an example of the invention being described is the LabVIEW™ software available from National Instruments Corporation.

FIRST EXAMPLE

FIG. 2 illustrates the apparatus 10 in more detail. In this example, the arbitrary waveform generator 12 is based on a software package such as that described above, running on a computer device 22. The computer device 22 may be a conventional PC or other computer device including processing apparatus 24, input devices such as a keyboard 26 and output devices such as a display 28. The software 29 running in the processing apparatus 24 allows the generator 12 to provide a representation of the waveform on the display 28. The user inputs, such as the keyboard 26, allow a user to define the parameters of the waveform represented on the display 28. For example, the user may choose the shape and frequency of the represented waveform, or other parameters. Thus, the user manipulates a digital representation within the computer device 22.

Fine control of the waveform shape is expected to be improved if the software creates the waveform as a time series of discrete samples. If each sample can be individually manipulated, considerable control can be provided for the user when defining the shape of the waveform. This degree of control is enhanced as the sample rate increases. We envisage using a sample rate of at least 100 MS/s (million samples per second). This allows samples at 10 times the frequency of a 10 MHz waveform, for a 10 MHz transducer.

The computer device 22 incorporates, or has associated with it, a digital-to-analogue convertor 30. When the waveform defined by the user is to be used, the computer device 22 uses the converter 30 to provide a signal to the power amplifier 16, at 32. The signal at 32 represents the waveform defined by the user. Examples will be described below.

At this stage of the process, signals will be at low voltage and low power, typical of voltage and power levels found within conventional computer devices such as the device 22 and signal processor circuits such as the digital-to-analogue convertor 30. For example, a waveform at 32 may have an amplitude of 1 V (2 V peak-to-peak). The purpose of the power amplifier 16 is to receive the waveform output at 32, at low voltage and low power levels, and to amplify the waveform output 32 in power and amplitude. For example, we envisage the power amplifier 16 amplifying the waveform output 32 from an amplitude of 1 V (2 V, peak-to-peak) to an amplitude of 10 V (20 V, peak-to-peak).

In this example, the power amplifier 16 is based around an operational amplifier 34 and also includes appropriate conventional ancillary circuits such as power supplies (not shown).

In this specification, the term “operational amplifier” is used to refer to one of a class of devices which provide very high gain voltage amplification. Gain may be many thousands. The devices have two inputs and a single output which represents the voltage difference between the inputs, multiplied by the gain of the device. That is, the operational amplifier has a differential input. Various feedback techniques allow the overall gain to be dictated by external components and to be highly independent of the operating conditions. We envisage that the use of an operational amplifier will provide the advantage that the signal from the arbitrary signal generator can be amplified in amplitude and power, with minimal degradation of the shape of the waveform. Other characteristics of operational amplifiers which contribute to the low level of signal degradation in the circumstances being described include high bandwidth, high linearity, low noise, short rise time and high slew rate, which may generally be termed “high speed”. One example of an appropriate operational amplifier circuit is a non-inverting operational amplifier configuration using the THS3001™ device available from Texas Instruments Inc.

The output of the operational amplifier 34 forms the power output 18 of the power amplifier 16 and is supplied to the ultrasonic transducer 20. Accordingly, when the apparatus 10 is in use, the arbitrary waveform which has been created under user control within the computer device 22 is converted to an analogue form at the converter 30, amplified from signal levels at 32 to power levels at 18 by the operational amplifier 34, and then used by the ultrasonic transducer 20 to create ultrasound.

An example of an ultrasonic transducer is a lead zirconate titanate piezo ceramic transducer.

In use, the transducer 20 will be associated with a workpiece 36, usually by placing the transducer 20 into intimate contact with the workpiece 36 to provide good transfer of ultrasound from the transducer 20 into the body of the workpiece 36. In the illustrated example, the transducer 20 is also used to collect reflected ultrasound (echo) from the workpiece 36, which is passed through an appropriate interface circuit 38 and analogue-to-digital converter 40 to be received by the computer device 22 for recording and analysis. In an alternative, separate transducers may be used to create ultrasound and to detect echoes. This may help block the transmitted ultrasound from directly affecting the echo receiving transducer. The possibility of separate transducers is indicated in FIG. 2 by a broken line dividing the transducer 20.

We envisage that the use of an arbitrary waveform generator 12, such as a generator based on an appropriate software package, will allow the waveform output 14 to have very high quality, because of the precise control available to the user when defining the shape of the waveform. We envisage that the waveform output 14 will have a high signal-to noise ratio. Furthermore, we envisage that the use of an operational amplifier 34 will allow the power and amplitude to be amplified (to create the power output 18) while retaining a high signal-to-noise ratio. Consequently, the ultrasound which is ultimately introduced to the workpiece 36 is expected to have sufficient power to penetrate the workpiece 36, create reflections and other interactions, and thus reveal information about the workpiece 36, and to do so in a manner which provides high-quality output (and thus high-quality information). This arises from the high signal-to-noise ratio in the initial waveform, the precision with which the waveform is initially shaped, and because the operational amplifier introduces minimal degradation of the waveform. These results are expected even if the ratio of the output waveform amplitude to the received echo amplitude may be less than in conventional ultrasonic systems. Precise shaping of the waveform, perhaps in complicated shapes, is expected to reveal information which cannot be obtained from conventional ultrasound generation techniques. Examples include high precision measurement of a dimension or feature of a workpiece.

FIG. 3 illustrates waveforms appearing at various points in the apparatus. FIG. 3 (*a*) illustrates a time series of discrete output values 42 representing samples of a generally sinusoidal waveform. Individual manipulation of each of these samples (including the height and polarity of the sample) provides a high level of control over the waveform shape, particularly at a high sample rate, such as at least 100 MS/s and at least 10 times the frequency of the waveform. At this stage, the waveform is represented purely in a digital representation within the generator 12, and will be available to the user, through the display 28.

FIG. 3 (*b*) shows the output of the converter 30 after receiving the waveform samples of FIG. 3 (*a*). As can be seen, the analogue waveform, forming the waveform output 14, has the approximately sinusoidal shape defined by the samples of FIG. 3 (*a*) and is at relatively low power and amplitude (1V; 2V peak-to-peak). This waveform is then applied to the power amplifier 16, to provide the power output 18, illustrated at FIG. 3 (*c*) in truncated form. The waveform of FIG. 3 (*c*) has the same shape as the waveform of FIG. 3 (*b*), but has been amplified to a greater power and amplitude (20 V peak-to-peak), while retaining the high signal-to-noise ratio of the earlier waveforms. This quality of the waveform is made possible by the use of the operational amplifier 34.

FIG. 4 illustrates an example waveform which we have found to be advantageous in ultrasonic non-destructive testing. The waveform 44 includes two pulses 46, 48 which are a generating pulse 46 and a damping pulse 48. The generating pulse 46 is a pulse of a high frequency carrier on which a generally sinusoidal amplitude envelope is imposed. The damping pulse 48 is also a pulse of the high frequency carrier, and also in a generally sinusoidal amplitude envelope.

The purpose of the generating pulse 46 is to excite the transducer 20 to generate ultrasound in the workpiece 36. We have found that stimulating a transducer 20 with a sinusoidal pulse such as the pulse 46 can result in resonance effects within the transducer 20, which may cause the ultrasound vibrations in the workpiece 36 to be longer than the signal provided to the transducer 20. An example is indicated at 47. The purpose of the damping pulse 48 is to address this issue. The timing and phase of the damping pulse 48 can be chosen to cause the damping pulse 48 to damp any residual resonance within the transducer 20. In particular, it is desirable for the transducer 20 to be damped before the time at which reflected ultrasound is expected to be received from within the workpiece 36, so that the transducer 20 is quiescent when the reflection is received. This is expected to result in the recovery of higher quality signals from the workpiece 36.

SECOND EXAMPLE

Figure 5:
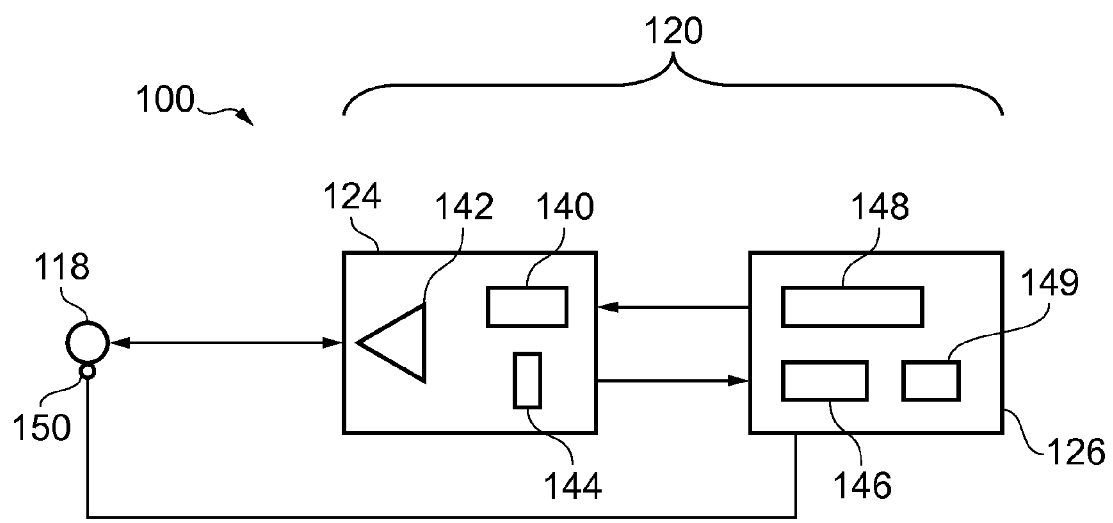
FIG. 5 is a simple schematic diagram of an alternative ultrasound generating apparatus.

An alternative ultrasound generating system 100 is depicted schematically in FIG. 5. The system 100 shares many features in common with the apparatus 10. The system 100 includes an ultrasonic transceiver 118, and a control system 120 including a pulse generation module 124 and a controller module 126.

The ultrasonic transducer 118 comprises a piezoelectric transducer which is fixed in use to an item under test (not shown) using a fixing such as glue. If desired, the ultrasonic transducer might be deposited in situ on the surface of the item. The fixing selected depends primarily on the item and the conditions it is expected to experience in use, but needs to enable good transmission of ultrasound signals over the temperature range expected in use. When fixed in place the sensor may be covered with a backing to assist in transmitting the ultrasonic signal to the item, such as an epoxy resin backing, for example steel reinforced epoxy. The transducer 118 has a centre frequency of approximately 10 MHz, although other frequencies are possible.

The pulse generation module 124 is operable to generate a voltage pulse having a peak amplitude of approximately 10V. The pulse generation module includes a pulse generator 140, an amplifier 142 and a signal blocker 144 (if required). The pulse generator is operable to generate a voltage pulse of substantially 1V which has a repeatable shape. In this example the pulse comprises a square wave which physically manifests itself as a sine wave with a frequency of substantially 10 MHz, and the pulse generator 140 comprises a first programmable element such as a field programmable gate array (FPGA 1). As well as generating the initial pulse to be transmitted, the FPGA 1 is operable to receive the reflected signal.

In this example, the amplifier 142 is operable to amplify the shaped signal produced by the FPGA 1 to approximately a 10V pulse without altering the frequency or shape. If such a high voltage signal were received by the FPGA 1, then it would damage the FPGA 1. Therefore, when the amplifier is active the signal blocker 144, which in this example is a field-effect transistor (FET), is activated simultaneously to ensure that no portion of the 10V signal can be transmitted back towards the FPGA 1. As soon as the amplifier has transmitted the 10V pulse, the signal blocker 144 is deactivated to allow the reflected signal to be detected by the FPGA 1.

In another example, separate transducers may be used for generating ultrasound and for sensing echoes, as noted above in relation to FIG. 2. If so, a natural block is created between the excitation energy and the sensing transducer, which may make the signal blocker 144 unnecessary.

The controller module 126 includes a further programmable element 146 such as a second field programmable gate array (FPGA 2) and a processor 148, and a memory 149. The FPGA 2 is operable to collect temperature data from a temperature sensor 150, such as a thermocouple, arranged to measure the temperature of the item under test.

The processor 148 is in signal communication with both programmable elements 140 and 146, and receives signal data from FPGA 1 and temperature data from FPGA 2. The processor uses the received signal data and temperature data to produce a dimensional measurement.

In operation, the system 100 performs the following two sets of operations substantially simultaneously under control of the processor.

Firstly, programmable element 140 generates a 1V pulse 50 ns in duration. The signal blocker 144 is activated, and the amplifier 142 amplifies the 1V pulse to 10V. The signal blocker is then deactivated. The 10V signal is transmitted to the ultrasonic transceiver 118 over a cable. The ultrasonic transceiver converts the signal to an ultrasonic pulse, and transmits the pulse into the item under test. A reflected ultrasonic pulse is subsequently received by the ultrasonic transceiver, converted to an electrical signal, and detected by the programmable element 140. Data identifying the received signal (and in particular a collection of discrete measurements which together are indicative of the shape of the received signal) is transmitted to the processor for analysis/storage, and in particular for generation of a time of flight value.

Simultaneous with the above collection of time of flight data, the processor instructs the second programmable element 146 to collect temperature data from the temperature sensor 150. A measured temperature value (which consists of two measurements) is stored in memory until FPGA 1 has collected the received signal. These operations are arranged to start and finish substantially synchronously.

Once the signal data has been collected, the processor determines a time of flight which is calibrated using the temperature value. A temperature independent dimensional value is then calculated. That value is indicative of a dimension, such as the thickness of the item under test.

CONCLUDING COMMENTS

We have found that fine tuning and manipulation of the shape of the waveform, allows the waveform shape to be selected to create increased echo amplitude, when expressed as a percentage of the amplitude introduced, as compared with conventional techniques. This represents a higher efficiency and arises from the ability to generate arbitrary waveforms, and to amplify them accurately and repeatably in the operational amplifier.

Many variations can be made from the apparatus described above, without departing from the scope of the invention. For example, other forms of arbitrary waveform generator could be used in place of the generator based on a software package. Other forms of power amplifier could be used and other operational amplifier devices could be chosen according to conventional considerations in signal processing and circuit design.

Whilst endeavouring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

What is claimed is:

1. Ultrasound generating apparatus suitable for ultrasonic measurement of a dimension of a workpiece, comprising:

a generator operable to provide a waveform output representing a waveform;

a power amplifier operable to receive the waveform output and to amplify the waveform output to provide an output for applying to an ultrasonic transducer;

wherein the generator is an arbitrary waveform generator comprising a computing device operating as a waveform source under software control and providing a representation of the waveform and having user inputs operable to define parameters of the waveform represented, and a converter operable to provide the waveform output as a signal having the waveform of the representation, and wherein the power amplifier comprises an operational amplifier which, in use, receives the waveform output from the generator and amplifies the waveform output in power and in voltage, the output of the operational amplifier being applied to the transducer.

2. Apparatus according to claim 1, wherein the waveform output, in use, is a time series of discrete output values have samples of the waveform.

3. Apparatus according to claim 2, wherein the discrete outputs have a sample rate of at least 10 times the frequency of the waveform, such as 100 MS/s.

4. Apparatus according to claim 1, wherein the representation is a digital representation, and the converter is a digital-to-analogue convertor.

5. Apparatus according to claim 1, wherein the generator is operable to provide a waveform output as a pulse of a carrier frequency.

6. Apparatus according to claim 1, wherein the generator is operable to provide a waveform output as a pulse for generating ultrasound and followed by a damping pulse for damping resonance in an ultrasonic transducer.

7. A method of generating ultrasound for ultrasonic measurement of a dimension of a workpiece, comprising the steps of:

generating a waveform output representing a waveform;

amplifying the waveform output to provide an output for applying to an ultrasonic transducer;

wherein the waveform is generated by an arbitrary waveform generator comprising a waveform source provided by a computing device operating under software control and providing a representation of the waveform and having user inputs operable to define parameters of the waveform represented, and a converter operable to provide the waveform output as a signal having the waveform of the representation, and wherein the waveform is amplified by a power amplifier which comprises an operational amplifier which, in use, receives the waveform output from the waveform source and amplifies the waveform output in power and in voltage, the output of the operational amplifier being applied to the transducer.

8. A method according to claim 7, wherein the waveform output is generated as a time series of discrete output values and samples of the waveform.

9. A method according to claim 8, wherein the discrete outputs have a sample rate of at least 10 times the frequency of the waveform, such as 100 MS/s.

10. A method according to any of claim 7, wherein generating the waveform includes providing a waveform output as a pulse of a carrier frequency.

11. A method according to any of claim 7, wherein generating the waveform includes providing a waveform output as a pulse for generating ultrasound and followed by a damping pulse for damping resonance in an ultrasonic transducer.

* * * * *